United States Patent
Mohammad et al.

(10) Patent No.: US 9,156,763 B1
(45) Date of Patent: Oct. 13, 2015

(54) PHOTOCATALYST FOR SELECTIVE OXIDATION OF ALCOHOLS: A GREEN SYNTHESIS APPROACH

(71) Applicant: King Fahd University of Petroleum and Minerals, Dhahran (SA)

(72) Inventors: Qamar Mohammad, Dhahran (SA); Khalid Rashed Alhooshani, Dhahran (SA); Rami Bahaeldin Elsayed, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 14/530,867

(22) Filed: Nov. 3, 2014

(51) Int. Cl.
*B01J 19/12* (2006.01)
*C07C 45/29* (2006.01)

(52) U.S. Cl.
CPC ............... *C07C 45/29* (2013.01); *B01J 19/123* (2013.01); *B01J 19/127* (2013.01); *B01J 2219/1203* (2013.01)

(58) Field of Classification Search
CPC . C07C 45/29; B01J 19/123; B01J 2219/1203; B01J 19/127; C01B 25/41
USPC ................ 204/157.63, 157.93; 423/299–323; 422/108
See application file for complete search history.

(56) References Cited

U.S. PATENT DOCUMENTS

| | | | |
|---|---|---|---|
| 3,878,074 A * | 4/1975 | Reichenbacher et al. | 204/157.93 |
| 4,152,230 A * | 5/1979 | Edwards et al. | 204/157.87 |
| 4,655,891 A * | 4/1987 | Ward et al. | 204/157.93 |
| 2013/0123546 A1 * | 5/2013 | Carner Roda et al. | 204/157.93 |

FOREIGN PATENT DOCUMENTS

| | | |
|---|---|---|
| CN | 101648139 B | 5/2011 |
| CN | 101940937 B | 4/2012 |

OTHER PUBLICATIONS

Wang et al, "In situ synthesis of Ag3PO4/cellulose nanocomposites with photocatalytic activities under sunlight," Cellulose (2014) 21:3371-3382.*

Hou et al, "Ag3PO4 Oxygen Evolution Photocatalyst Employing Synergistic Action of Ag/AgBr Nanoparticles and Graphene Sheets," J. Phys. Chem. C, (2012), v. 116, pp. 20132-20139.*

Zhai et al, "Silver Phosphate/Carbon Nanotube-Stabilized Pickering Emulsion for Highly Efficient Photocatalysis," J. Phys. Chem. C, (2013), v. 117, pp. 15183-15191.*

Guo et al, "A new heterojunction Ag3PO4/Cr—SrTiO3 photocatalyst towards efficient elimination of gaseous organic pollutants under visible light irradiation," Applied Catalysis B: Environmental, vol. 134-135 (2013), pp. 286-292.*

(Continued)

*Primary Examiner* — Keith Hendricks
*Assistant Examiner* — Colleen M Raphael
(74) *Attorney, Agent, or Firm* — Oblon, McClelland, Maier & Neustadt, L.L.P.

(57) ABSTRACT

A photocatalyst comprising silver orthophosphate ($Ag_3PO_4$) is used for selective and exhaustive conversion of alcohols into their corresponding carbonyl compounds; namely, benzyl alcohol, 4-methoxy benzyl alcohol and/or cinnamyl alcohol with >99% yield. The reactions were carried out in double distilled water at room temperature and pressure under sunlight-type excitation. Oxidation of alcohols is selective and $Ag_3PO_4$ may be active for a variety of other essential oxidation reactions.

16 Claims, 7 Drawing Sheets

(56) References Cited

OTHER PUBLICATIONS

Guo et al, "An Ag3PO4/nitridized Sr2Nb2O7 composite photocatalyst with adjustable band structures for efficient elimination of gaseous organic pollutants under visible light irradiation," Nanoscale, 2014, vol. 6, pp. 7303-7311.*

Ren et al, "2D Porous graphitic C3N4 nanosheets/Ag3PO4 nanocomposites for enhanced visible-light photocatalytic degradation of 4-chlorophenol," J. Nanopart. Res. (2014) 16:2532.*

Rawal et al, "Novel Ag3PO4/TiO2 composites for efficient decomposition of gaseous 2-propanol under visible-light irradiation," Catalysis Communications 17 (2012) pp. 131-135.*

Yan et al., "Morphology-controlled synthesis of Ag3PO4 microcubes with enhanced visible-light-driven photocatalytic activity", vol. 39, Issue 8, Dec. 2013 (Abstract only).

Bettoni et al., "Selective photocatalytic oxidation at TiO2/Ti anodes of 4-methoxybenzyl alcohol to the corresponding benzaldehyde in "green" conditions", vol. 222, Issue 1, Jul. 2011 (Abstract only).

Spasiano et al., "TiO2/Cu(ll) photocatalytic production of benzaldehyde from benzyl alcohol in solar pilot plant reactor", vol. 136-137, Jun. 5, 2013 (Abstract only).

\* cited by examiner

PHOTOCATALYST FOR SELECTIVE OXIDATION OF ALCOHOLS: A GREEN SYNTHESIS APPROACH

STATEMENT OF ACKNOWLEDGEMENT

This project was funded by the National Plan for Science, Technology and Innovation (MAARIFAH)—King Abdulaziz City for Science and Technology—the Kingdom of Saudi Arabia, award number (10-NAN1387-04).

BACKGROUND OF THE INVENTION

1. Technical Field

The present disclosure relates to a method for the selective oxidation of alcohols into their corresponding carbonyl compounds using $Ag_3PO_4$ as a photocatalyst to oxidize at least 90% of the alcohols into their corresponding carbonyl compounds.

2. Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Selective, efficient and complete oxidation of alcohols into corresponding carbonyl compounds, such as aldehydes, ketones etc., is of paramount significance for chemical industries because carbonyl compounds are used in food, beverage, and pharmaceutical industries as well as a raw material in chemical industries (Miyamura, H.; Matsubara, R.; Miyazaki, Y.; Kobayashi, S. Angew. Chem. 2007, 119, 4229; Hundlucky, M. Oxidations in Organic Chemistry, American Chemical Society, Washington, D.C., 1990—each incorporated herein by reference in its entirety). To achieve the aforementioned conversions, the use of stoichiometric inorganic reagents, such as $KMnO_4$, $K_2CrO_4$ etc., is predominantly used in these industries. Although such reagents offer high activity and selectivity, accumulation of waste products arising from the use of these inorganic reagents poses a threat to the environment. Intensive effort has been carried out in past years to develop 'green oxidation processes'. Although there are active heterogeneous metal catalysts being developed for the aerobic oxidation of various alcohols, the reactions are carried out in harmful organic solvents and/or under vigorous conditions (Kwon, M. S.; Kim, N.; Park, C. M.; Lee, J. S.; Kang, K. Y.; Park, J. Org. Lett. 2005, 7, 1077; Enache, D. I.; Edwards, J. K.; Landon, P.; Solsona-Espriu, B.; Carley, A. F.; Herzing, A. A.; Watanabe, M.; Kiely, C. J.; Knight, D. W.; Hutchings, G. J. Science 2006, 311, 362; Yamada, Y. M. A.; Arakawa, T.; Hocke, H.; Uozumi, Y. Angew. Chem. 2007, 119, 718—each incorporated herein by reference in its entirety).

Since the discovery of water splitting on $TiO_2$ electrode in 1970 under light (Fujishima, A.; Honda, K. Nature 1972, 238, 37—incorporated herein by reference in its entirety), the photocatalytic process has been widely investigated owing to its renewable attributes. Most of the earlier studies involving photocatalysis focused on environmental cleanup, $H_2$ production, $CO_2$ reduction etc. (Hoffmann, M. R.; Martin, S. T.; Choi, W.; Bahnemann, D. W. Chem. Rev. 1995, 95, 69; Maeda, K.; Teramura, K.; Lu, D.; Takata, T.; Saito, N.; Inoue, Y.; Domen, K. Nature 2006, 440, 295; Varghese, O. K.; Paulose, M.; LaTempa, T. J.; Grimes, C. A. Nano Lett. 2009, 9, 731—each incorporated herein by reference in its entirety).

Recently, utilization of the photocatalytic process for the synthesis of fine chemicals in an environmentally friendly fashion is desirable (Yoon, T. P.; Ischay, M. A.; Du, J. Nature Chemistry 2010, 2, 527; Palmisano, G.; Augugliaro, V.; Pagliaro, M.; Palmisano, L. Chem. Commun. 2007, 3425—each incorporated herein by reference in its entirety). Attempts have been made to achieve various functional group transformations such as amine to imine (Lang, X. J.; Ji, H. W.; Chen, C. C.; Ma W. H.; Zhao, J. C. Angew. Chem. Int. Ed. 2011, 50, 3934; Su, F. Z.; Mathew, S. C.; Mohlmann, L.; Antonietti, M.; Wang, X. C.; Blechert, S. Angew. Chem. Int. Ed. 2011, 50, 657; Wang, C.; Xie, Z. G.; deKrafft, K. E.; Lin, W. B. J. Am. Chem. Soc. 2011, 133, 13445—each incorporated herein by reference in its entirety), nitro to azo (Zhu, H.; Ke, X.; Yang, X.; Sarina, S.; Liu, H. Angew. Chem. Int. Ed. 2010, 49, 9657—incorporated herein by reference in its entirety), aniline to azobenzene conversion (Li, S.; Diebold, U. J. Am. Chem. Soc. 2010, 132, 64—incorporated herein by reference in its entirety), hexane to hexanone and hexanol (Ide, Y.; Kawamoto, N.; Bando, Y.; Hattori, H.; Sadakane, M.; Sano, T. Chem. Commun. 2013, 49, 3652—incorporated herein by reference in its entirety), alcohols to their corresponding aldehydes (Yurdakal, S.; Palmisano, G.; Loddo, V.; Augugliaro, V.; Palmisano, L. J. Am. Chem. Soc. 2008, 130, 1568; Maldotti, A.; Molinari, A.; Amadelli, R. Chem. Rev. 2002, 102, 3811; Palmisano, G.; Garcia-Lopez, E.; Marci, G.; Loddo, V.; Yurdakal, S.; Augugliaro, V.; Palmisano, L. Chem. Commun. 2010, 46, 7074; Augugliaro, V.; Caronna, T.; Loddo, V.; Marc, G.; Palmisano, G.; Palmisano, L.; Yurdakal, S. Chem Eur. J. 2008, 14, 4640; Wang, Q.; Zhang, M.; Chen, C.; Ma, W.; Zhao, J. Angew. Chem. Int. Ed. 2010, 49, 7976; Palmisano, G.; Yurdakal, S.; Augugliaro, V.; Loddo, V.; Palmisano, L. Adv. Synth. Catal. 2007, 349, 964—each incorporated herein by reference in its entirety), and so on. Selective oxidation of alcohols into corresponding aldehydes is one of the indispensable transformations in organic synthesis because aldehydes are being used in food, beverage, and drug industries as well as raw materials in chemical industries. Examples of the photocatalysts that are studied for alcohol oxidation include CdS/graphene (Zhang, N.; Zhang, Y.; Pan, X.; Fu, X.; Liu, S.; Xu, Y-J. J. Phys. Chem. C 2011, 115, 23501—incorporated herein by reference in its entirety), CdS/graphene (Zhang, N.; Zhang, Y.; Pan, X.; Yang, M.-Q.; Xu, Y.-J. J. Phys. Chem. C 2012, 116, 18023—incorporated herein by reference in its entirety), and $Au/CeO_2$ (Tanaka, A.; Hashimoto, K.; Kominami, H. Chem. Commun. 2011, 47, 10446; Tanaka, A.; Hashimoto, K.; Kominami, H. J. Am. Chem. Soc. 2012, 134, 14526—each incorporated herein by reference in its entirety).

Xu et. al., studied the conversion of benzyl alcohol into benzaldehyde in the presence of CdS assembled on two-dimensional graphene scaffold under visible light in organic solvent (namely benzotrifluoride). Although the selectivity was ~80%, the conversion and the yield were <50%. Furthermore, Xu et. al., synthesized a ternary photocatalyst involving $CdS/graphene/TiO_2$ for the oxidation of benzyl alcohol to benzaldehyde and demonstrated that the ternary had better photocatalytic activity as compared to binary CdS/graphene. The conversion of benzyl alcohol was ~80% while selectivity towards benzaldehyde and yield of benzaldehyde were ~80% and <80% respectively, but the reaction was carried out in the organic solvent benzotrifluoride.

Kominami et. al. deposited Au nanoparticles on a $CeO_2$ photocatalyst surface and studied photocatalytic chemoselective oxidation of alcohols to their corresponding aldehydes caused by plasmonic effect of Au under irradiation by green light. Although high selectivity (>99%) and a complete (>99%) oxidation of benzyl alcohol to benzaldehyde was obtained, the rate of reaction or benzaldehyde formation was extremely low (3.0 µmolh$^{-1}$). In addition, disparate forms of $TiO_2$, namely rutile,[1] anatase, and brookite (Addamo, M.; Augugliaro, V.; Bellardita, M.; Paola, A. D.; Loddo, V.; Palmisano, G.; Palmisano, L.; Yurdakal, S. *Catal. Lett.* 2008, 126, 58—incorporated herein by reference in its entirety), and surface modified $TiO_2$, such as $Nb_2O_5/TiO_2$ (Furukawa, S.; Shishido, T.; Teramura, K.; Tanaka, T. *ACS Catal.*, 2012, 2, 175—incorporated herein by reference in its entirety), and $Pt/TiO_2$ (Zhai, W.; Xue, S.; Zhu, A.; Luo, Y.; Tian, Y. *ChemCatChem.* 2011, 3, 127—incorporated herein by reference in its entirety), have been investigated and it has been found that the rutile form is the most selective photocatalyst for the oxidation of the alcohol to its corresponding aldehyde.

In most of the studies, organic solvents were used to achieve high selectivity. The highest conversion and selectivity in water, which was 50% and 65% respectively, for the oxidation of alcohol to its corresponding aldehyde has been reported with rutile $TiO_2$ under UV light irradiation at room temperature.

The development of active catalysts for selective and efficient conversion of alcohols to aldehydes in energy efficient and environmentally benign ways is highly desirable by chemical industries. The current disclosure describes the selective (>99%) and the exhaustive conversion (>90%) of benzyl alcohol and 4-methoxy benzyl alcohol to their corresponding aldehydes, namely benzaldehyde and 4-methoxybenzaldehyde respectively, with >99% yield, photocatalyzed by $Ag_3PO_4$ in water at room temperature and pressure under sunlight-type excitation. Moreover, >90% conversion of cinnamyl alcohol to cinnamaldehyde with >90% selectivity and >90% yield is also achieved in aqueous suspension of $Ag_3PO_4$ at room temperature and pressure under sunlight-type excitation.

BRIEF SUMMARY OF THE INVENTION

The foregoing paragraphs have been provided by way of general introduction, and are not intended to limit the scope of the following claims. The described embodiments, together with further advantages, will be best understood by reference to the following detailed description taken in conjunction with the accompanying drawings.

One embodiment of the disclosure describes a method for the selective oxidation of alcohols into their corresponding carbonyl compounds.

In another embodiment the method includes irradiating a mixture comprising a benzyl alcohol and an $Ag_3PO_4$ catalyst to oxidize the alcohol into its corresponding carbonyl compound.

In another embodiment the irradiating is carried out with a combination of UV and visible light.

In another embodiment at least 99% of benzyl alcohol is oxidized to benzaldehyde.

In another embodiment at least 99% of 4-methoxybenzyl alcohol is oxidized to 4-methoxybenzaldehyde.

In another embodiment at least 90% of cinnamyl alcohol is oxidized to cinnamaldehyde.

In another embodiment the irradiating is carried out with light of <5% UV and <40% visible light.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Referring now to the drawings, wherein like reference numerals designate identical or corresponding parts throughout the several views.

In the present disclosure silver orthophosphate ($Ag_3PO_4$) is used as a photocatalyst for the selective (>99%) and the exhaustive conversion (>90%, preferably >95%, >98% or >99%) of selected alcohols including benzyl alcohol, 4-methoxy benzyl alcohol and cinnamyl alcohol, to their corresponding aldehydes with >99% yield. The reactions were carried out in double distilled water at room temperature and pressure under sunlight-type excitation. Although oxidation of few selected alcohols were demonstrated, $Ag_3PO_4$ is likely to be active for a variety of other essential oxidation reactions.

First, to form the catalyst, a first inorganic compound containing hydrogen, phosphate, and a group 1 cation is dissolved in double distilled water. The first inorganic compound used can be any of the following including but not limited to $Na_2HPO_4$, $K_2HPO_4$, or $Li_2HPO_4$. Preferably the first inorganic compound is $Na_2HPO_4$. After the first inorganic compound is dissolved in water, a second inorganic compound, $AgNO_3$, is added to the water to create a first mixture. Upon addition of the second inorganic compound to the water, a bright yellow precipitate is immediately formed. The first mixture is mixed to complete the reaction. Manual methods and mechanical methods may be used to mix the solution. Mechanical methods include but are not limited to sonicating the solution using an ultrasonic bath or an ultrasonic probe or ultrasonicating the solution. Preferably the mixture is stirred for a time period in the range of 15-90 minutes, 35-80 minutes, or 58-70 minutes to complete the reaction. Preferably, the first mixture is stirred for a time period of 60 minutes to complete the reaction.

Upon completion of stirring, the resulting product is collected by centrifugation. The product is then washed with water and a solvent including but not limited to ethanol, methanol, or propanol. Preferably the solvent is ethanol. The product is then dried overnight at a temperature in the range of 75-110° C., 80-100° C. or 85-95° C. Preferably the product is dried overnight for a period of 12 hours at a temperature of 90° C.

The photocatalytic activity of $Ag_3PO_4$ was evaluated using an immersion well photochemical reactor comprising Pyrex glass, a magnetic stirring bar, a water circulating jacket and openings for supply of gases. A sample solution comprising the alcohols including but not limited to benzyl alcohol, 4-methoxy benzyl alcohol and cinnamyl alcohol is taken into the photo-reactor. The solution has a volume in the range of 100-200 mL, 110-190 mL, or 120-180 mL. Preferably, the solution has a volume of 130 mL. The solution is then stirred in the dark for a period of 15-100 minutes, 20-80 minutes, or 30-60 minutes. Preferably, the solution is stirred in the dark for at least 15 minutes to allow equilibration of the system to occur. A zero time reading is taken from the solution before the solution is exposed to light. The irradiation process is carried out a tungsten halogen lamp having a power of at least 230W and emits more than 5% UV light and less than 40% visible light in order to create a sunlight-type excitation. Preferably the experiment is carried out under conditions at room temperature. Temperature control is maintained by circulating water through the outer jacket of the reactor to prevent the reactor from allowing the temperature to rise. Samples in a volume of at least 3 mL are collected before irradiation and at regular hourly time intervals during irradiation for a time period of at least 1-8 hours. The catalyst is removed by filtration. The amount of catalyst used is in the range of 0.1-10 g/L, 0.5-5 g/L, or 0.75-3 g/L. Preferably the amount of catalyst used is in the range of 0.75-3 g/L.

The irradiated solutions are extracted by 3 mL of chloroform in three portions at a volume of at least 1 mL each. The extracted samples are analyzed by gas chromatography mass spectrometry. Concentrations of alcohols and aldehydes are determined from the peak areas.

The alcohol is oxidized such that the carbonyl product formed by the oxidation is mainly a single compound. Preferably the carbonyl product formed by the oxidation represents at least 95%, preferably 98% or 99% of a single carbonyl compound. The reaction occurs such that a single isomer of the carbonyl product is formed and at least 90% of a single isomer of the carbonyl product is formed, preferably 98% or 99% of a single isomer of the carbonyl product is formed. Temperature and pressure control are maintained so that the temperature is preferably room temperature (e.g., 20-25° C.) and the pressure is preferably ambient pressure (e.g., 0.985-1.015) atm.

EXAMPLES

Figure 1:
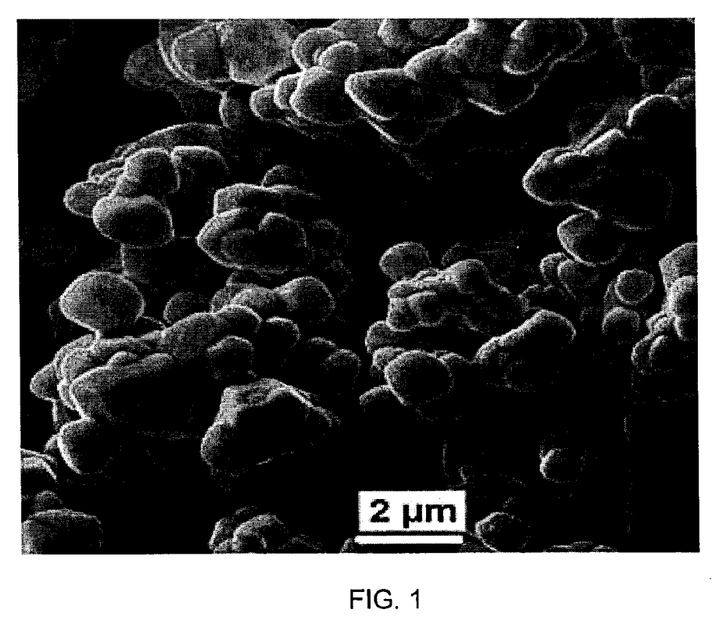
FIG. 1 is an illustration of a field emission scanning electron microscopic image of $Ag_3PO_4$.
Figure 2:
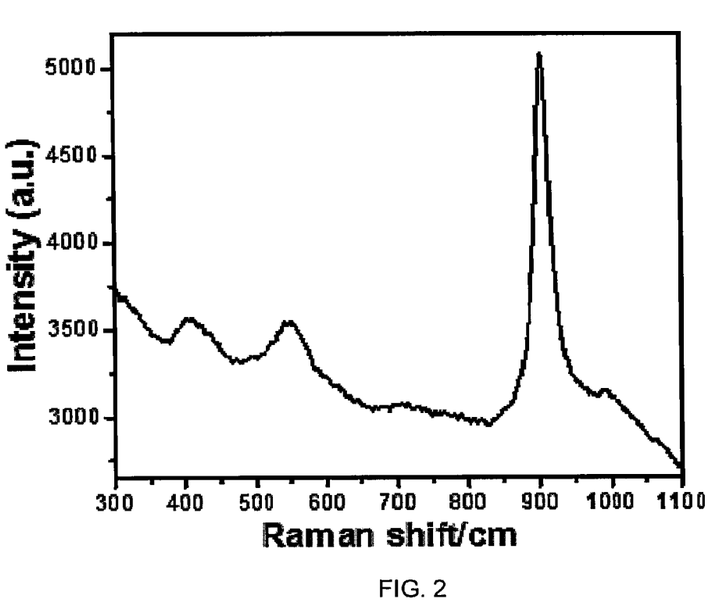
FIG. 2 is a graph of a raman spectrum of $Ag_3PO_4$.

In a typical synthesis, required amounts of $Na_2HPO_4$ was dissolved in double distilled water followed by addition of $AgNO_3$. A bright yellow precipitate was immediately formed and resulting suspension was kept under stirring for 1 h for a complete reaction. The product was collected by centrifugation, washed several time with water and ethanol and was dried at 90° C. for overnight. FIG. 1 depicts a field emission scanning electron microscopic image of $Ag_3PO_4$. Particle agglomerates of the $Ag_3PO_4$ have sharp-faceted features of fractured surfaces and have an average particle size of from 0.5 to 2 µm. In other embodiments the average particle size of the $Ag_3PO_4$ particles is from 0.8 to 1.5 µm. FIG. 2 is a raman spectrum of $Ag_3PO_4$.

The photocatalytic activity of $Ag_3PO_4$ for oxidation of alcohols was evaluated using immersion well photochemical reactor made of Pyrex glass equipped with a magnetic stirring bar, a water circulating jacket and with openings for supply of gases. A detailed schematic of photocatalytic reactor was presented in our previous paper (Qamar. M.; Muneer, M. *J. Hazard. Mater.* 2005, 120, 219—incorporated herein by reference in its entirety). For irradiation experiment, 130 mL solution was taken into the photo-reactor and required amount of photocatalyst was added and the solution was stirred for at least 15 min in the dark to allow equilibration of the system so that the loss of compound due to adsorption, if any, could be taken into account. The zero time reading was obtained from the solution withdrawn before the light was turned on. Irradiations were carried out using a 230 W tungsten halogen lamp which emits <5% UV light and <40% visible light (a sunlight-type excitation). The temperature was controlled and kept at room temperature by circulating water through outer jacket of reactor. Samples (3 mL) were collected before and at regular intervals during the irradiation and the catalyst was removed by filtration.

Figure 3:
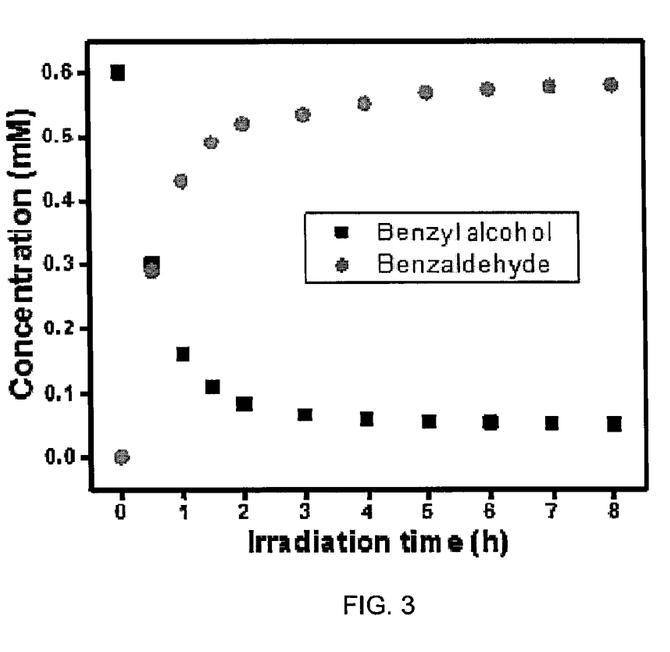
FIG. 3 is a graph of the conversion of benzyl alcohol into benzaldehyde with respect to irradiation time.
Figure 4:
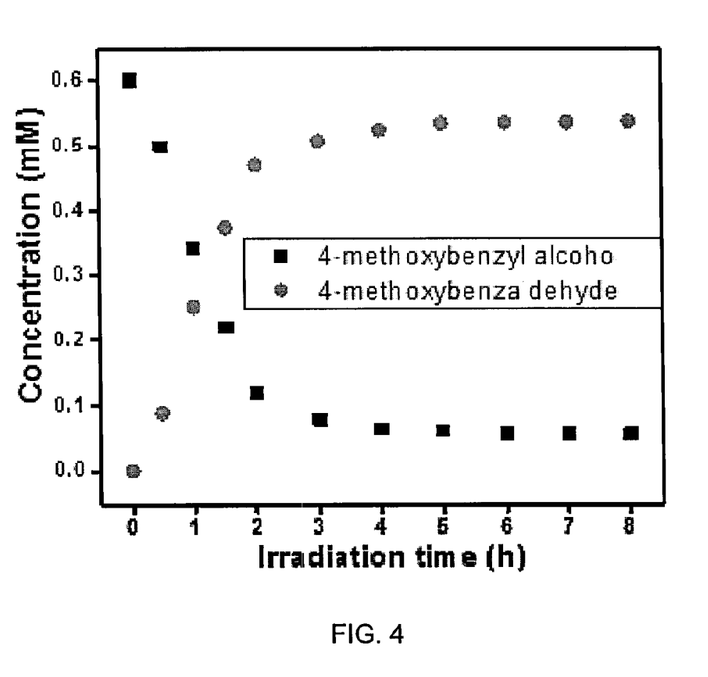
FIG. 4 is a graph of the conversion of 4-methoxybenzyl alcohol into 4-methoxybenzaldehyde with respect to irradiation time.
Figure 5:
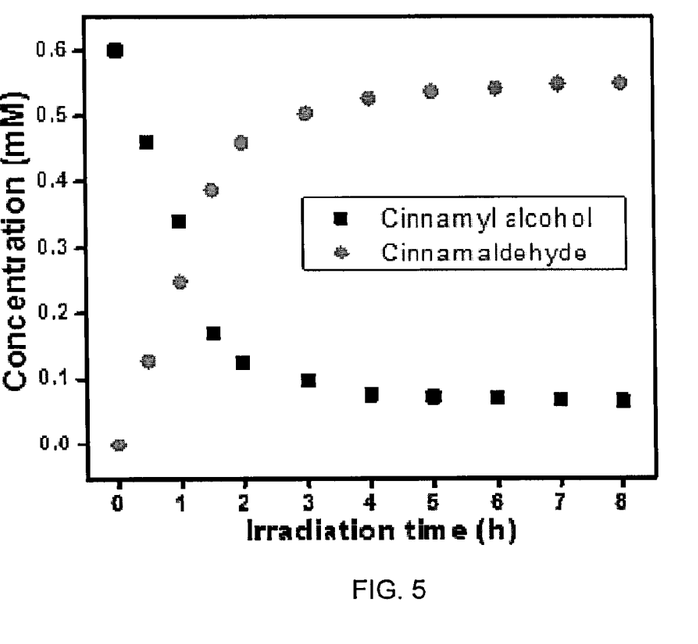
FIG. 5 is a graph of the conversion of cinnamyl alcohol into cinnamaldehyde with respect to irradiation time.

The properties of the conversion of alcohols into their corresponding carbonyl compounds with respect to irradiation time is illustrated in FIG. 3-FIG. 5. FIG. 3 is a graph of the conversion of benzyl alcohol into benzaldehyde with respect to irradiation time (Experimental conditions: $Ag_3PO_4$=2 $gL^{-1}$, alcohol concentration=0.6 mM, Irradiation time=8 h, Volume ($H_2O$)=130 mL). FIG. 4 is a graph of the Conversion of 4-methoxybenzyl alcohol into 4-methoxybenzaldehyde with respect to irradiation time (Experimental conditions: $Ag_3PO_4$=2 $gL^{-1}$, alcohol concentration=0.6 mM, Irradiation time=8 h, Volume ($H_2O$)=130 mL). FIG. 5 is a graph of the conversion of cinnamyl alcohol into cinnamaldehyde with respect to irradiation time (Experimental conditions: $Ag_3PO_4$=1 $gL^{-1}$, alcohol concentration=0.6 mM, irradiation time=8 h, volume ($H_2O$)=130 mL).

Figure 6:
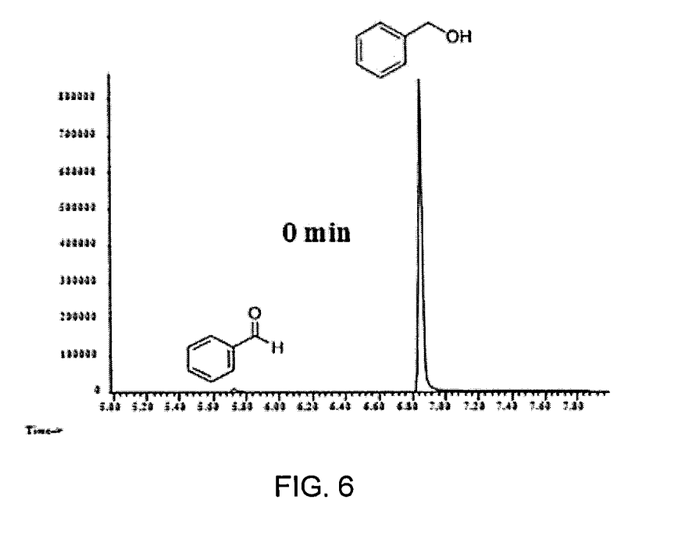
FIG. 6 is a GC-MS spectra of benzyl alcohol before photocatalytic treatment.
Figure 7:
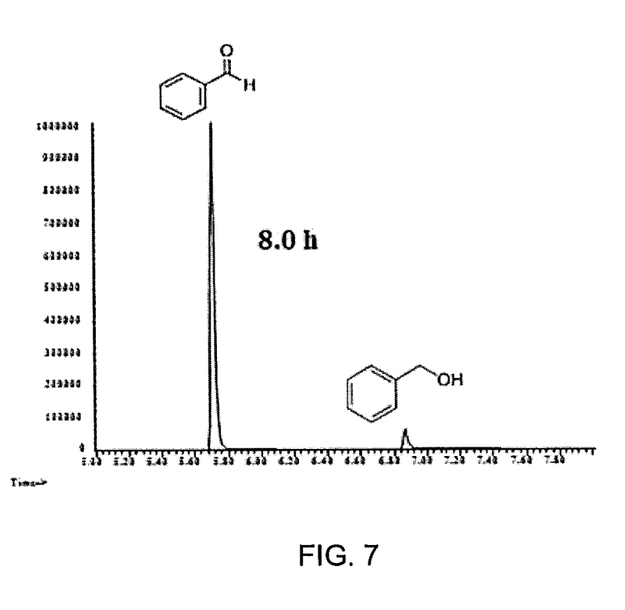
FIG. 7 is a GC-MS spectra of benzyl alcohol solution after photocatalytic treatment.

All the irradiated solutions were extracted by 3 mL of chloroform in three portions, 1 ml each, for maximum extraction. Analysis of the extracted samples was carried out by gas chromatography mass spectrometer using Agilent HP-5 (5% phenyl methyl siloxan, "30 m, 320 um, 0.25 um") capillary column. Selected ion monitoring mode (SIM) was used for routine analysis. Programming of the GC oven temperature was as follows: it was set to reach 40° C. in 1 min then 10° C./min to reach 200° C. Injection volume was 100 mL with split ratio 2:1. The calibration curves were obtained by injecting standards solutions of reactants and products, such as benzyl alcohol, benzaldehyde, 4-methoxy benzyl alcohol, and 4-methoxy benzaldehyde and so. The concentrations of alcohols and aldehydes were determined from the peak areas. FIG. 6 and FIG. 7 are GC-MS spectra of benzyl alcohol before and after photocatalytic treatment, respectively. FIG. 6 is a GC-MS spectra of benzyl alcohol before photocatalytic treatment. FIG. 7 is a GC-MS spectra of benzyl alcohol solution after 8 h of photocatalytic treatment showing the consumption of benzyl alcohol and the formation of benzaldehyde.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, define, in part, the scope of the foregoing claim terminology such that no inventive subject matter is dedicated to the public.

The invention claimed is:
1. A method for the selective oxidation of alcohols into their corresponding carbonyl compounds comprising:
   irradiating an aqueous mixture comprising an alcohol and a catalyst, which is $Ag_3PO_4$, to oxidize the alcohol and form a carbonyl compound, wherein:
   the irradiating is carried out with a combination of UV and visible light.
2. The method of claim 1, wherein the $Ag_3PO_4$ catalyst is in the form of particles suspended in the aqueous mixture.

3. The method of claim 2, wherein the $Ag_3PO_4$ catalyst comprises $Ag_3PO_4$ particles having an average particle size ranging from 0.5 to 2 μm.

4. The method of claim 2, wherein the $Ag_3PO_4$ catalyst consists of $Ag_3PO_4$ particles.

5. The method of claim 1, wherein the alcohol is oxidized to selectively form a product mixture which contains more than 95% of a single carbonyl compound.

6. The method of claim 1, wherein the aqueous mixture comprises a liquid phase that consists of water and the alcohol.

7. The method of claim 1, wherein the alcohol is 4-methoxybenzyl alcohol, cinnamyl alcohol, or benzyl alcohol.

8. The method of claim 1, wherein at least 99% of benzyl alcohol is oxidized to benzaldehyde.

9. The method of claim 1, wherein at least 99% of 4-methoxybenzyl alcohol is oxidized to 4-methoxybenzaldehyde.

10. The method of claim 1, wherein at least 90% of cinnamyl alcohol is oxidized to cinnamaldehyde.

11. The method of claim 1, wherein the irradiating is carried out with more than 5% UV light and less than 40% visible light.

12. The method of claim 1, wherein the irradiation is performed for a time period of from 1 to 8 hours.

13. The method of claim 1, wherein the irradiation is performed for a time period of from 3 to 8 hours.

14. The method of claim 1, wherein an amount of the $Ag_3PO_4$ catalyst used is from 0.1 to 10 g per 1 L of an aqueous solution comprising the alcohol.

15. The method of claim 1, wherein the alcohol is oxidized to selectively form a product mixture which comprises more than 90% of a single isomer of the carbonyl compound.

16. The method of claim 1, wherein the aqueous mixture comprises mainly water.

* * * * *